United States Patent [19]

Needham et al.

[11] 4,250,341
[45] Feb. 10, 1981

[54] 2,2,6,6-TETRACHLORO (OR BROMO) CYCLOHEXANE AND PYROGALLOL

[75] Inventors: Brian J. Needham; John Miller, both of Cambridge, England

[73] Assignee: Fisons Limited, London, England

[21] Appl. No.: 56,973

[22] Filed: Jul. 12, 1979

[30] Foreign Application Priority Data

Jul. 12, 1978 [GB] United Kingdom ............... 29563/78

[51] Int. Cl.³ ...................... C07C 37/01; C07C 37/02; C07C 49/403
[52] U.S. Cl. .................................... 568/361; 568/376; 568/763
[58] Field of Search ...................... 260/586 R; 568/763

[56] References Cited

U.S. PATENT DOCUMENTS

| | | | |
|---|---|---|---|
| 2,116,893 | 5/1938 | Heisel | 260/586 R |
| 2,674,572 | 4/1954 | Gundel et al. | 260/586 R |
| 3,360,565 | 12/1967 | Arnoldy | 260/586 R |
| 3,385,902 | 5/1968 | Bright et al. | 260/586 R |
| 3,988,369 | 10/1976 | Pearson | 260/586 R |

*Primary Examiner*—Joseph E. Evans
*Attorney, Agent, or Firm*—Wenderoth, Lind & Ponack

[57] ABSTRACT

The intermediate 2,2,6,6-tetrachloro (or tetrabromo) cyclohexanone is prepared by reacting chlorine (or bromine) with a cyclohexanol compound of the formula

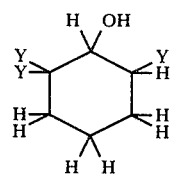

where each Y represents an atom of hydrogen or chlorine (or hydrogen or bromine) in the presence of, as catalyst, a certain organophosphorus compound.

10 Claims, No Drawings

2,2,6,6-TETRACHLORO (OR BROMO) CYCLOHEXANE AND PYROGALLOL

This invention relates to a process for preparing 2,2,6,6-tetrachlorocyclohexanone or 2,2,6,6-tetrabromocyclohexanone.

These two compounds have uses particularly as intermediates, e.g. in the portion of pyrogallol or a salt thereof by hydrolysing either of them. We have now discovered a surprisingly useful process for preparing the compounds.

Accordingly, the invention provides a process for preparing 2,2,6,6-tetrachlorocyclohexanone or 2,2,6,6-tetrabromocyclohexanone, which comprises reacting, in the case of the production of 2,2,6,6-tetrachlorocyclohexanone, chlorine, and in the case of the production of 2,2,6,6-tetrabromocyclohexanone, bromine, with a cyclohexanol compound of the formula

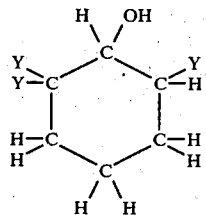

I where each Y is the same or different and represents, the case of the production of 2,2,6,6-tetrachlorocyclohexanone, an atom of hydrogen or chlorine, and in the case of the production of 2,2,6,6-tetrabromocyclohexanone, an atom of hydrogen or bromine, in the presence of, as catalyst, an organophosphorus compound of the formula

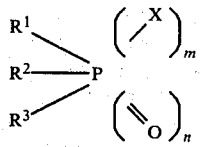

II where X represents an atom of chlorine or bromine; n is 0 or 1; and when n is 0, m is 0 or 2, $R^1$ is alkyl of 1 to 10, e.g. 1 to 6, carbon atoms or phenyl, and $R^2$ and $R^3$ are the same or different and are hydrogen, alkyl of 1 to 10, e.g. 1 to 6, carbon atoms or phenyl; and when n is 1, m is 0, and $R^1$, $R^2$ and $R^3$ are the same and each is

alkyl of 1 to 10, e.g. 1 to 6, carbon atoms or phenyl, or $R^1$ is hydrogen and $R^2$ and $R^3$ are the same or different and each is alkyl of 1 to 10, e.g. 1 to 6, carbon atoms or phenyl;

or a salt of such an organophosphorus compound.

The present process produces the product readily, in high yield and in a high state of purity. The process is particularly useful when the product is to be hydrolysed to pyrogallol or a salt thereof, and especially when the pyrogallol or salt thereof is to be reacted with 2,2-dimethoxypropane and the 2,2-dimethyl-4-hydroxy-1,3-benzodioxole product reacted with methyl isocyanate to produce the pesticide bendiocarb, 2,2-dimethyl-1,3-benzodioxol-4-yl methylcarbamate.

Any alkyl group in the catalyst is usually of 1–4 carbon atoms, particularly methyl, ethyl or n-butyl, though it may also be of 8 carbon atoms, especially 2-ethylhexyl or n-octyl. When there is more than one alkyl group in the molecule, they are conveniently the same.

In a particular embodiment, n is 1 and $R^1$, $R^2$ and $R^3$ are each

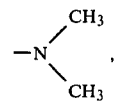

i.e. the catalyst is hexamethylphosphoramide or a salt thereof.

In a preferred embodiment, the catalyst is a tertiary phosphine, e.g. dimethylethylphosphine, tri-n-octylphosphine or tri(2-ethylhexyl)-phosphine, or a salt thereof, and especially tributylphosphine, triphenylphosphine, or a salt of either. References to tributylphosphine are to tri-n-butylphosphine.

In another preferred embodiment, the catalyst is a phosphine oxide, particularly a tertiary phosphine oxide, especially triphenylphosphine oxide.

In a particular embodment, m is 0.

The catalyst may be provided as the organophosphorus compound itself or as a salt of this compound where a salt exists. Thus, the reaction may be carried out in the presence of acid salts of the catalysts. Suitable acids include both inorganic acids, such as Lewis acids (e.g. boron trifluoride) or mineral acids (e.g. hydrochloric or sulphuric acid), or organic acids, such as carboxylic acids containing up to 10 carbon atoms (e.g. acetic acid or propionic acid). The salt may be a quaternary phosphonium salt.

The nature of the acid portion of the salt is not particularly significant; it is the basic portion of the catalyst which is important. Moreover, copious quantities of hydrochloric or hydrobromic acid (depending on whether chlorine or bromine is used) are normally produced in the course of the reaction, so that a substantial portion of the catalyst is generally present as the hydrochloric or hydrobromic acid salt regardless of the particular ingredient used as source of the catalyst.

In a particular embodiment, 2,2,6,6-tetrachlorocyclohexanone is prepared and the catalyst is provided in the form of hydrochloric acid salt, e.g. tributylphosphine hydrochloride or triphenylphosphine hydrochloride. Conveniently hydrogen chloride gas is passed into tributylphosphine or triphenylphosphine in 2,2,6,6-tetrachlorocyclohexanone or carbon tetrachloride, and the salt formed is used as catalyst in the chlorination to produce 2,2,6,6-tetrachlorocyclohexanone.

The catalyst may be chlorinated or brominated during the course of the reaction, and the acid portion of the acid salt catalyst, particularly salts of organic acids, may be chlorinated or brominated during the course of the reaction. Thus, if the catalyst is provided as a phosphine (n is 0 m is 0 in the formula above), it may well be chlorinated to and function as the dichloro derivative. For instance, tributylphosphine or triphenylphosphine may be converted to and function as $Bu_3PCl_2$ or Ph₃PCl₂ respectively. The catalyst may be provided as such a chlorinated or brominated derivative. In the case of chlorination with tributylphosphine or triphenylphosphine, however, this is not preferred since the dichloro derivatives tend to be unstable.

When the catalyst is provided as a phosphine (n is 0 and m is 0 in the formula above), it may well be oxidised during the course of the reaction to and function as a phosphine oxide (n is 1 in the formula above). For instance, if the catalyst is provided as tributylphosphine or triphenylphosphine or a salt of either, it may well be chlorinated to the corresponding dichloro derivative and then converted to the corresponding tributylphosphine oxide or triphenylphosphine oxide. The catalyst may be provided as such a phosphine oxide.

Preferably the catalyst is provided to the reaction mixture as an organophosphorus compound of formula II wherein m is 0 or a salt thereof.

Especially preferred is providing the catalyst to the reaction mixture as tributylphosphine or a salt thereof, triphenylphosphine or a salt thereof, tributylphosphine oxide or triphenylphosphine oxide. References to tributylphosphine oxide are to tri-n-butylphosphine oxide.

The catalyst may be a mixture of the organophosphorus compounds but this is not preferred.

The amount of catalyst is not critical, but generally its weight is at least 0.1%, preferably from 0.5 to 12%, of the weight of the cyclohexanol compound.

The compounds of formula I employed as starting materials in the process are either known compounds, or may be prepared by methods well known to those skilled in the organic chemical synthesis for the preparation of analogous compounds.

The process is of particular interest for the prodution of 2,2,6,6-tetrachlorocyclohexanone, so that the halogen involved is chlorine rather than bromine and Y represents an atom of hydrogen or chlorine rather than an atom of hydrogen or bromine.

The cyclohexanol compound is preferably cyclohexanol itself, though an intermediately halogenated compound may be employed, e.g. 2-chlorocyclohexanol, 2,2-dichlorocyclohexanol or 2,6-dichlorocyclohexanol.

The reaction is preferably conducted in the liquid phase.

The reaction is preferably conducted in the presence of a solvent. Suitable solvents include saturated chlorinated hydrocarbons (e.g. aliphatic hydrocarbons containing 1 or 2 carbon atoms and 2-4 chlorine atoms, such as carbon tetrachloride, methylene dichloride, 1,2-dichloroethane or tetrachloroethanes), saturated hydrocarbons (e.g. those containing 5-10 carbon atoms such as pentane, hexane, cyclohexane, octane or decane), saturated carboxylic acids (e.g. saturated alphatic carboxlic acids containing 2-5 carbon atoms, such as acetic acid, propionic acid or butanoic acid) or water. The use of water as sole solvent, however, is not preferred. Preferably, the solvent is molten desired product, e.g. 2,2,6,6-tetrachlorocyclohexanone, itself. A mixture of solvents can be employed but this is not preferred.

In a preferred mode of operation, the halogen and cyclohexanol are fed to a reaction zone containing a solvent and the catalyst.

The reaction is usually conducted at a temperature within the range 0°–160° C., preferably 40°–110° C. The reaction temperature is preferably below the boiling point of the solvent if a solvent is employed. When molten 2,2,6,6-tetrachlorocyclohexanone is employed as solvent, the minimum reaction temperature is its melting point as altered by the other materials present. The melting point of pure 2,2,6,6-tetrachlorocyclohexanone is 82°–83° C.

Preferably 2,2,6,6-tetrachlorocyclohexanone is prepared by reacting chlorine with cyclohexanol, in the liquid phase, at a temperature of 0°–160° C., in a process in which there is provided, as catalyst for the reaction, an organophosphorus compound of the formula

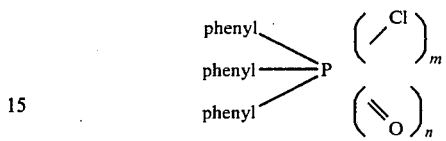

wherein n is 0 or 1; and
when n is 0, m is 0 or 2, and when n is 1, m is 0;
or a salt of such an organophosphorus compound.

The overall amount of chlorine or bromine employed is normally sufficient to convert all the cyclohexanol compound to desired product. When the reaction is conducted by feeding the halogen and cyclohexanol compound to a reaction zone containing a solvent and the catalyst, it is preferred, in order to minimise side reactions, the amount of the halogen in contact with the cyclohexanol compound in the reaction zone be at all times at least the stoichiometric amount required to convert the cyclohexanol compound present in the desired product. For instance, starting from cyclohexanol, there may be for example at least 2, preferably at least 5 moles, of halogen fed per mole of cyclohexanol fed; desirable, 5-6 moles of halogen are fed while each mole of cyclohexanol is fed.

The desired product can be separated in conventional ways. It can be used without purification to produce pyrogallol or a salt thereof by hydrolysis, but the product can be purified if desired by conventional techniques, e.g. by recrystallisation, vacuum distillation or sublimation. The hydrolysis is described for example in cognate United Kingdom patent specification 49142/75, 32007/76 and 44318/76.

Thus, pyrogallol forms salt by reason of its phenolic OH groups. The pyrogallol produced by the hydrolysis can be in the form of its salts. The salts include particularly alkali metal, e.g. sodium or potassium, especially sodium, salts and can be prepared from pyrogallol itself in conventional ways, e.g. by reaction with alkali metal alkoxides. Pyragallol itself can be prepared from its salts in conventional ways, e.g. by reaction with acid, for example hydrochloric acid.

Usually pyrogallol itself rather than a salt thereof is formed in the hydrolysis, and the pyrogallol can be converted to a salt thereof if desired though this is not preferred.

The hydrolysis may be considered over all:

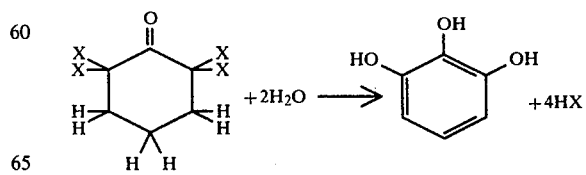

where each X is the same and represents a chlorine or bromine atom, preferably a chlorine atom.

The hydrolysis can be effected directly or indirectly. Direct hydrolysis is the reaction of the tetrahalocyclohexanone compound itself with water. Indirect hydrolysis is the reaction of the tetrahalocyclohexanone compound to form a derivative which is reacted with water in a separate stage. Indirect hydrolysis can be carried out for example by reacting the tetrahalocyclohexanone compound with a metal (e.g. sodium, potassium, calcium or aluminum) alkoxide (e.g. derived from an alkanol of 1–4 carbon atoms), preferably sodium methoxide, followed by acid hydrolysis, for example by hydrochloric acid. Direct hydrolysis, however, enables the overall reaction to be conducted in a smaller number of stages, and is preferred.

The yield in the direct hydrolysis can be improved dramatically by employing a catalyst. A wide range of materials act as catalysts in this respect. There can be used as catalyst a base or an anion. An anion is included within some definitions of a base, but in the present specification we prefer to differentiate between them. The base can be, for example, morpholine, triethanolamine, cyclohexylamine, di-n-butylamine or 2-(diethylamino)ethanol or an anion exchange resin.

The catalyst is preferably, however, an anion. Suitable anions include (A) the anionic part of a cation exchange resin (e.g. a carboxylic acid cation exchange resin) in the hydrogen or salt form (e.g. the sodium, potassium, calcium or ammonium form), e.g. Amberlite IRC 50 in the hydrogen or sodium form, or, preferably, (B) an anion of another salt (called herein a simple salt to differentiate it from the ion exchange resin salt), e.g. citrate, dihydrogen citrate, hydrogen citrate, acetate, monochloroacetate, hydrogen malate, malate, hydrogen phthalate, hydrogen isophthalate, hydrogen tartrate, tartrate, oxalate ($^{-}OOCCOO^{-}$), o-nitrobenzoate, benzoate, lactate, propionate, glycolate, malonate ($^{-OOCCH_2}COO^{-}$), formate, salicylate ($HOC_6H_4COO^{-}$), hydrogen adipate, adipate, hydrogen phosphate, dihydrogen phosphate, picolinate, furoate, dihydrogen pyrophosphate, hydrogen succinate, sulphamate, hydrogen phosphite, gluconate, borate ($H_2BO_3^{-}$) or fluoride.

The anion of a simple salt is preferably employed in the form of a simple salt rather than the acid. The anion catalyst can be in the form of water-soluble metal, ammonium, or amine, salt or a mixture thereof. The amine salt can be that of a primary, secondary or tertiary amine. The amine can be aliphatic, aromatic or heterocyclic or an amine containing a mixture of such substituents on the amine nitrogen atom. It is generally preferred to use the sodium, potassium, ammonium or morpholine salt. The salt can be admixed as such or it can be generated in situ, e.g. by reacting acid from which the salt is derived with alkali. For instance, cation exchange resin in the salt form can be generated in situ by providing the resin in the hydrogen form and having alkali present. Alternatively, the salt may be formed in situ by employing an ester, such as methyl oxalate, in the presence of an alkali.

Specific simple salts which are catalysts include trisodium citrate, mono-morpholine citrate, di-morpholine citrate, sodium dihydrogen citrate, disodium hydrogen citrate, sodium acetate, sodium chloroacetate, sodium hydrogen malate, disodium malate, sodium hydrogen phthalate, potassium hydrogen phthalate, ammonium hydrogen phthalate, sodium hydrogen isophthalate, sodium hydrogen tartrate, disodium tartrate, disodium oxalate, sodium o-nitrobenzoate, sodium benzoate, sodium lactate, sodium propionate, sodium glycolate, disodium malonate, sodium formate, monosodium salicylate, sodium hydrogen adipate, disodium adipate, disodium hydrogen phosphate, sodium dihydrogen phosphate, sodium picolinate, sodium furoate, disodium dihydrogen pyrophosphate, sodium hydrogen succinate, sodium sulphamate, sodium hydrogen phosphite, sodium gluconate, monosodium borate, and potassium fluoride.

In the case of a salt of a polybasic acid, a mixed salt, e.g. a sodium potassium salt, can be employed.

The anion catalyst is preferably an anion of a carboxylic acid. The carboxylic acid can be an aliphatic, aromatic, heterocyclic or alicyclic carboxylic acid. The carboxylic acid can contain one or more carboxyl groups. Where there is more than one carboxyl group, one is preferably neutralised but the others may or may not be. Where there is more than one carboxyl group, a mixed salt, e.g. a sodium potassium salt, can be employed. The carboxylic acid preferably contains only carbon, hydrogen and oxygen atoms. Especially preferred for convenience, availability and high yield is (a) a straight chain alkanoic acid of 1–6 carbon atoms, which alkanoic acid is optionally substituted by one or more groups selected from carboxyl and hydroxy groups, or (b) benzoic acid substituted by one or more groups selected from carboxyl and hydroxy groups.

The $pK_a$ of the acid whose anion may be employed is usually in the range 2.0–6.5, preferably 2.8–5.7.

Particularly preferred specific salts are sodium acetate, disodium hydrogen citrate, sodium hydrogen phthalate or sodium hydrogen adipate.

A mixture of catalysts can be employed.

The direct hydrolysis occurs at a pH of at least 2. For maximum yield, the pH is preferably 2.8–6.0. The hydrolysis produces hydrohalic acid HX, which can lower the pH below these lower limits. For optimum yield it is preferred to maintain the pH above these lower limits during the hydrolysis. This can be done by employing the catalyst in salt form as appropriate, e.g. as sodium salt, to raise the pH over what it would otherwise be, or by admixing alkali. The alkali can be any convenient alkali, such as alkali metal hydroxide, carbonate or bicarbonate, e.g. sodium carbonate, but preferably sodium hydroxide. Preferably the pH is maintained at 2.8–6.0 throughout the hydrolysis.

Although we are not bound by this theory, it seems that when an anion is used as catalyst, the hydrolysis may be considered in terms of one catalyst anion displacing each halogen atom X on the 2,2,6,6-tetrahalocyclohexanone compound and then each catalyst anion being itself displaced by an $HO^-$ ion from water, rearrangement occurring to result in the pyrogallol. It can be seen that this is analogous to the indirect hydrolysis mentioned above in which the tetrahalocyclohexanone compound is reacted with a metal alkoxide and the product is acid hydrolysed; there an alkoxide ion is the anion to displace each X atom, and the displacement of the alkoxide ion occurs in a separate stage.

When an anion is used as catalyst and the anion is that of a simple salt, the amount of catalyst is preferably at least 4 anions per molecule of tetrahalocyclohexanone. Better yields are generally obtained using 6–10 of the catalyst anions, than using 4 of the catalyst anions, per molecule of tetrahalocyclohexanone. Generally, no better yield is obtained using 16 of the catalyst anions than using 8 of the catalyst anions, per molecule of tetrahalocyclohexanone.

When an anion is used as catalyst and the anion is that of a cation exchange resin, the amount of catalyst is preferably at least 4 equivalents, especially 6–10 equivalents, of anion per mole of tetrahalocyclohexanone, generally no better yield being obtained using 16 rather than 8 equivalents of anion per mole of tetrahalocyclohexanone.

When a base is used as catalyst, it is thought, though we are not bound by their theory, that one equivalent of base reacts with one equivalent of hydrohalic acid produced in the hydrolysis. When a base is used as catalyst, the amount of catalyst is preferably at least 4 equivalents of base per mole of tetrahalocyclohexanone.

When the direct hydrolysis is used, an organic liquid, e.g. methanol or ethanol, may be employed in the reaction mixture to give a system which is initially of one phase rather than two phases.

The present hydrolysis is preferably conducted in solution. At least the theoretical quantity of water to effect the hydrolysis must be employed, and when direct hydrolysis is employed, the solvent is preferably water in excess of that required for hydrolysis. When direct hydrolysis is employed, preferably the whole of any catalyst is in solution.

When the alkoxide route mentioned above is employed, the reaction with the alkoxide is generally conducted in the presence, as solvent, of the alkanol from which the alkoxide is derived, and the subsequent acid hydrolysis may be conducted in the presence, as solvent, of water in excess of that required for hydrolysis.

Preferably the hydrolysis employs 0.3 ml–1 liter of water per gram of tetrahalocyclohexanone compound.

The hydrolysis may for example be conducted at a temperature of 0°–250° C., e.g. 0°–120° C. The reaction mixture is usually heated. In a preferred embodiment, particularly when direct hydrolysis is employed, the temperature is 60°–140° C. Preferably direct hydrolysis is conducted under reflux.

The hydrolysis may be conducted under a pressure which is above, at, or below atmospheric pressure. The pressure may for instance be 0.1–15 atmospheres, conveniently atmospheric pressure.

Pyrogallol and its salts absorb oxygen when hot, and the salts absorb oxygen even at ambient temperature. Accordingly, excessive heating of them should be avoided and it may be desirable in some instances to conduct the hydrolysis under an inert atmosphere, e.g. an atmosphere of nitrogen or carbon dioxide.

The product can be isolated and purified in conventional ways.

The invention is illustrated by the following Examples, in which parts are by weight and references to tetrachlorocylohexanone are to 2,2,6,6-tetrachlorocyclohexanone.

EXAMPLE 1

143 g $CCl_4$ and 1.25 g triphenylphosphine were charged to a 500 ml flask fitted with mechanical stirrer, thermometer, water condenser, chlorine inlet tube to the bottom of the flask and cyclohexanol inlet tube. With the $CCl_4$ at reflux temperature, 213 g $Cl_2$ and 50 g cyclohexanol containing 4.4 g water were charged to the flask continuously over 10 hours. The mole ratio of $Cl_2$ to cyclohexanol was kept at 6:1 throughout the addition and the temperature of the reaction rose generally to 85° C. At the end of the cyclohexanol feed, a further 10 g $Cl_2$ was added over 1 hour to complete the conversion of intermediate products to tetrachlorocyclohexanone. On cooling, the white crystalline product which formed weighed 143.5 g and contained 65% of tetrachlorocyclohexanone. Yield = 79%.

EXAMPLE 2

135 g tetrachlorocyclohexanone (87.2% pure) and 1.25 g triphenylphosphine were charged to a 500 ml flask fitted with mechanical stirrer, thermometer, water condenser, chlorine inlet tube to the bottom of the flask and cyclohexanol inlet tube. The tetrachlorocyclohexanone was melted and heated to 100° C., then fed continuously over 10 hours with 213 g $Cl_2$ and 50 g cyclohexanol containing 4.4 g water. The mole ratio of $Cl_2$ to cyclohexanol was kept at 6:1 throughout the addition and the temperature maintained at 95°–100° C. At the end of the cyclohexanol feed, a further 10 g $Cl_2$ was added over 1 hour to complete the conversion of intermediate products to tetrachlorocyclohexanone. On cooling, the white crystalline product which formed was 251 g of 88.6% pure tetrachlorocyclohexanone. 104.5 g tetrachlorocyclohexanone had been freshly formed in 88.5% yield.

EXAMPLE 3

As Example 1 using 0.75 g tri-n-butylphosphine instead of the triphenylphosphine.

There was 134.4 g of product containing 72% of tetrachlorocyclohexanone. 82% yield.

EXAMPLE 4

As Example 2 using 0.75 g tri-n-butylphosphine instead of the triphenylphosphine.

There was freshly formed 103 g tetrachlorocyclohexanone in 87.3% yield.

EXAMPLE 5

The following mixture was made up: cyclohexanol 100 parts, water 8.4 parts, carbon tetrachloride 127 parts, triphenyl phosphine 2.6 parts.

With good mechanical agitation, 310 parts of chlorine were added to the mixture via a dip tube over 4 hours at 30°–40° C. The mixture was then heated and a further 135 parts of chlorine added over 2.4 hours at 67°–93° C. The contents of the flask were sampled and analysed for tetrachlorocyclohexanone by an internal standard gas-liquid chromatographic method, indicating the presence of 203.5 parts of this product (86.2% yield).

EXAMPLE 6

As Example 2 using 1.3 g triphenylphosphine oxide instead of the triphenylphosphine.

There was freshly formed 110 g tetrachlorocyclohexanone in 93% yield.

EXAMPLE 7

As Example 1 using 5 g hexamethylphosphoramide instead of the triphenylphosphine.

There was freshly formed 107 g tetrachlorocyclohexane in 91% yield.

We claim:

1. A process for preparing 2,2,6,6-tetrachlorocyclohexanone or 2,2,6,6-tetrabromocyclohexanone, which comprises reacting in the liquid phase, in the case of the production of 2,2,6,6-tetrachlorocyclohexanone, chlorine, and in the case of the production of 2,2,6,6-tetrabromocyclohexanone, bromine, with a cyclohexanol compound of the formula

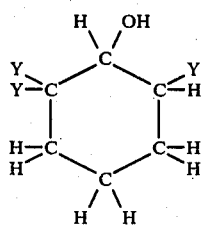

where each Y is the same or different and represents, in the case of the production of 2,2,6,6-tetrachlorocyclohexanone, an atom of hydrogen or chlorine, and in the case of the production of 2,2,6,6-tetrabromocyclohexanone, an atom of hydrogen or bromine, in the presence of as catalyst, an organophosphorus compound of the formula

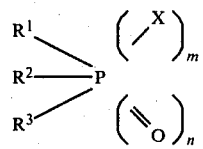

where
X represents an atom of chlorine or bromine;
n is 0 or 1; and
when n is 0, m is 0 or 2, $R^1$ is alkyl of 1 to 10 carbon atoms or phenyl, and $R^2$ and $R^3$ are the same or different and are hydrogen, alkyl of 1 to 10 carbon atoms or phenyl; and
when n is 1, m is 0, and $R^1$, $R^2$ and $R^3$ are the same and each is

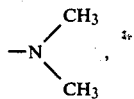

alkyl of 1 to 10 carbon atoms or phenyl, or $R^1$ is hydrogen and $R^2$ and $R^3$ are the same or different and each is alkyl of 1 to 10 carbon atoms or phenyl;
or a salt of said organophosphorus compound.

2. A process according to claim 1 wherein each alkyl group in formula II is of 1–6 carbon atoms.

3. A process according to claim 1 wherein n is 1 and $R^1$, $R^2$ and $R^3$ are each

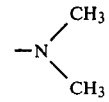

4. A process according to claim 1 wherein $R^1$, $R^2$ and $R^3$ are each phenyl.

5. A process according to claim 1 or 2 wherein m is 0.

6. A process according to claim 1 wherein 2,2,6,6-tetrachlorocyclohexanone is prepared.

7. A process according to claim 1 wherein the cyclohexanol compound is cyclohexanol itself.

8. A process according to claim 1 wherein the reaction is conducted at a temperature of 0°–160° C.

9. A process for preparing 2,2,6,6-tetrachlorocyclohexanone, which comprises reacting chlorine with cyclohexanol, in the liquid phase, at a temperature of 0°–160° C., in which process there is provided, as catalyst for the reaction, an organophosphorus compound of the formula:

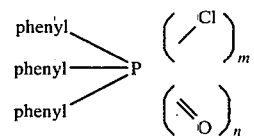

wherein
n is 0 or 1; and
when n is 0, m is 0 or 2 and when n is 1, m is 0;
or a salt of said organophosphorus compound.

10. A process for preparing pyrogallol or a salt thereof, which comprises carrying out the process according to claim 1, and hydrolysing the 2,2,6,6-tetrachlorocyclohexanone or 2,2,6,6-tetrabromocyclohexanone.

* * * * *